United States Patent [19]

McCormick

[11] Patent Number: 5,080,869
[45] Date of Patent: Jan. 14, 1992

[54] APPARATUS AND METHOD FOR PREPARING TISSUE SAMPLES FOR HISTOLOGICAL EXAMINATION

[76] Inventor: James B. McCormick, 6755 Longmeadow Dr., Lincolnwood, Ill. 60646

[21] Appl. No.: 567,274

[22] Filed: Aug. 14, 1990

[51] Int. Cl.5 .............................................. B01L 3/00
[52] U.S. Cl. ..................................... 422/102; 422/99; 435/299
[58] Field of Search .................. 422/99, 102; 211/126, 211/128, 187, 208; 118/500; 435/299, 300

[56] References Cited

U.S. PATENT DOCUMENTS

| | | | |
|---|---|---|---|
| 2,316,892 | 4/1943 | Saul, Jr. | 211/128 |
| 2,540,664 | 2/1951 | Gluckman | 211/128 X |
| 2,761,813 | 9/1956 | Goetz | 435/299 |
| 2,800,102 | 7/1957 | Welskopf et al. | 118/500 X |
| 2,837,055 | 6/1958 | Whitehead | 118/500 |
| 3,168,100 | 2/1965 | Rich | 118/500 X |
| 3,195,502 | 7/1965 | Levy | 118/500 |
| 4,421,246 | 12/1983 | Schultz et al. | 220/355 X |
| 4,569,647 | 2/1986 | McCormick | 422/99 X |
| 4,834,943 | 5/1989 | Yoshiyama | 118/500 X |

*Primary Examiner*—Robert J. Warden
*Assistant Examiner*—Stephanie Blythe
*Attorney, Agent, or Firm*—Fitch, Even, Tabin & Flannery

[57] ABSTRACT

The present invention is directed to a stackable cassette and apparatus for preparation of multiple tissue specimens for histological examination. The cassettes include a bottom wall, two side walls, a front wall and a back wall which define a cavity. The bottom wall has a plurality of apertures disposed therein for passage of fluid through the cassette in a direction orthogonal to the plane of the bottom wall. At least two walls selected from the back wall, two side walls and front wall have a plurality of apertures disposed therein for passage of fluid through the cassette in the direction parallel to the plane of the bottom wall. In one embodiment of the invention, the cassette further includes a web of porous material disposed over the apertures in the bottom wall and side walls. When the cassettes are placed in stacked relationship the bottom wall of an overlying cassette provides a cover for the underlying cassette.

22 Claims, 4 Drawing Sheets

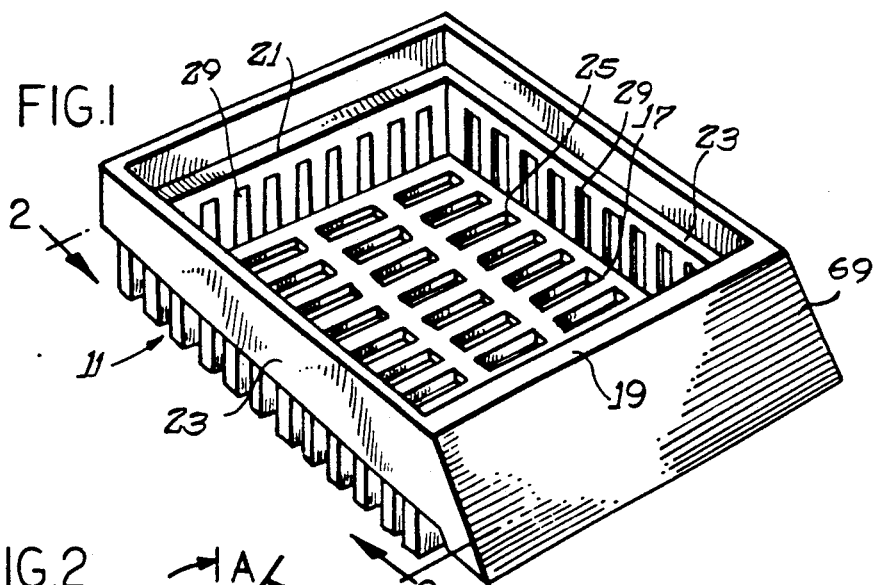
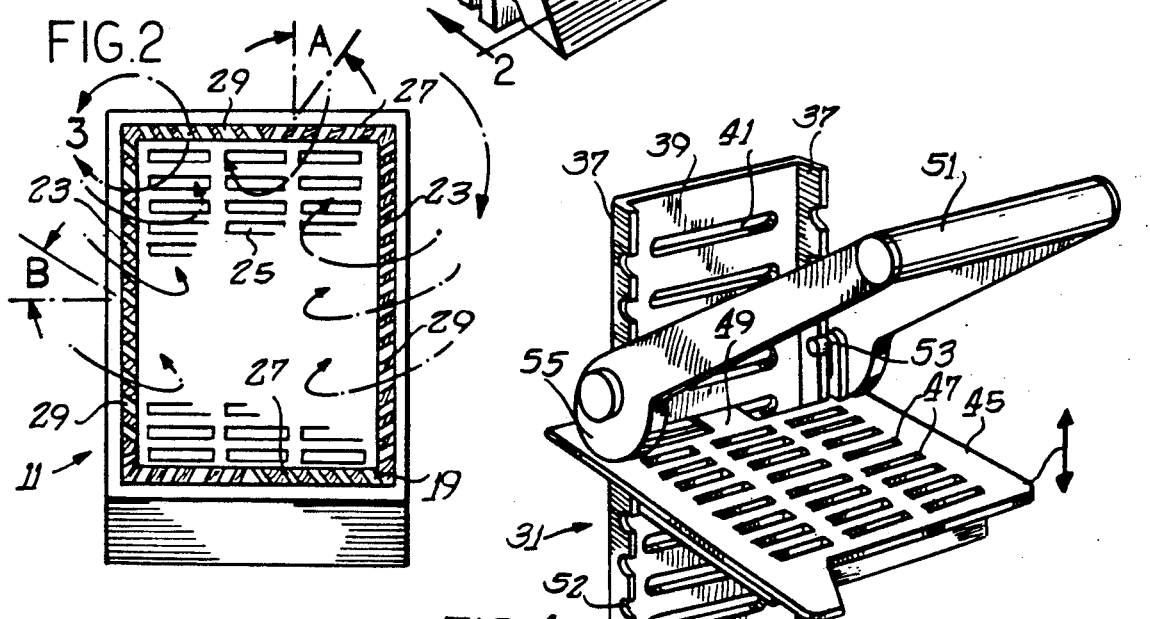
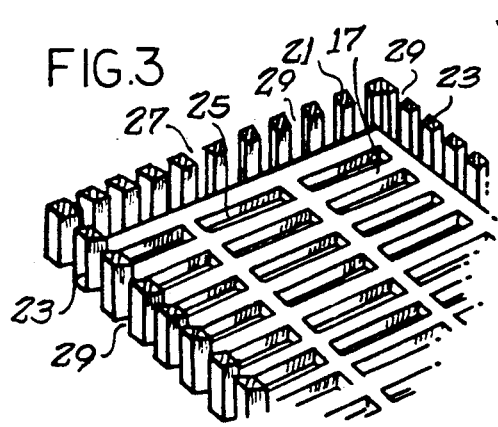
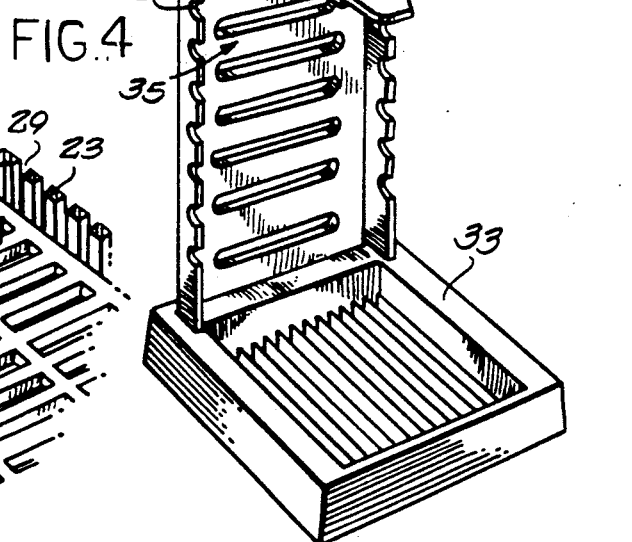

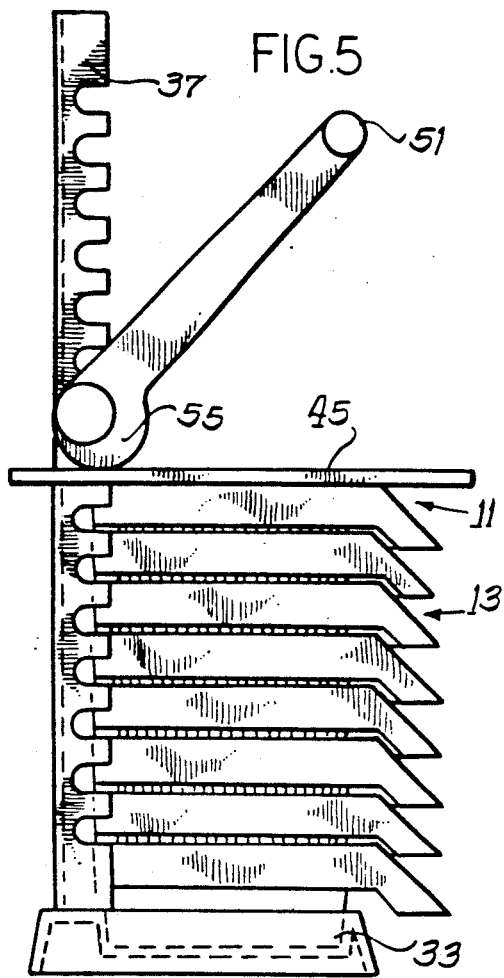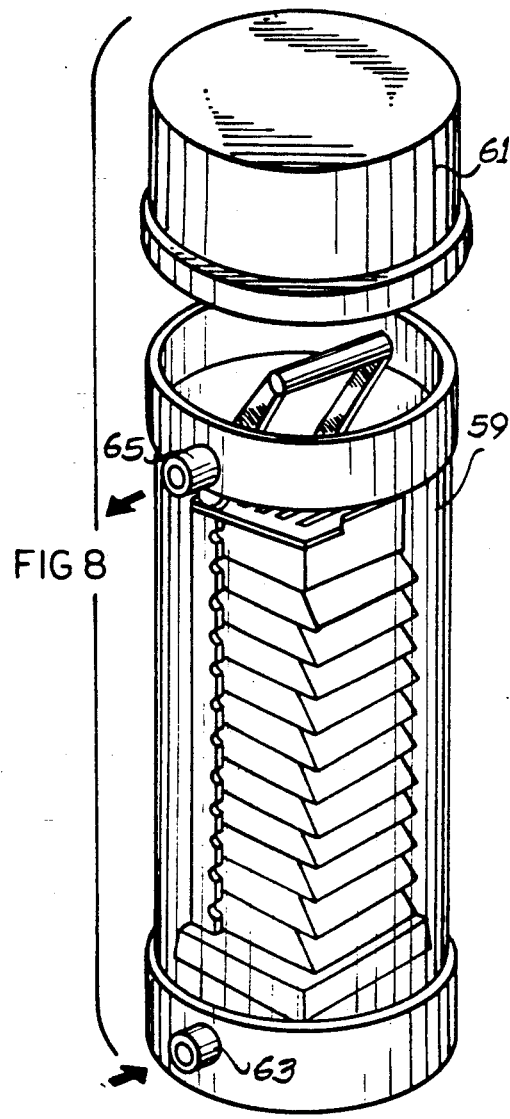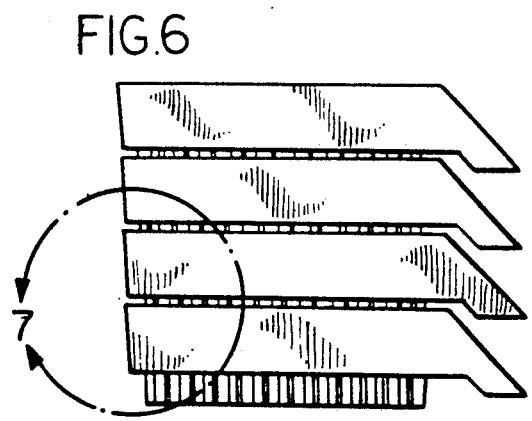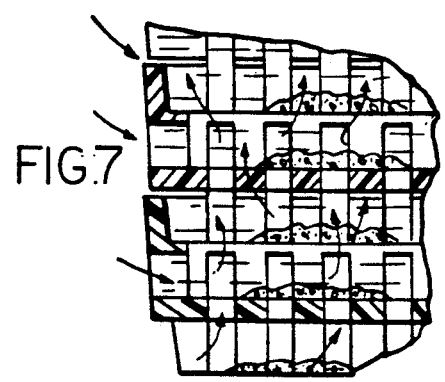

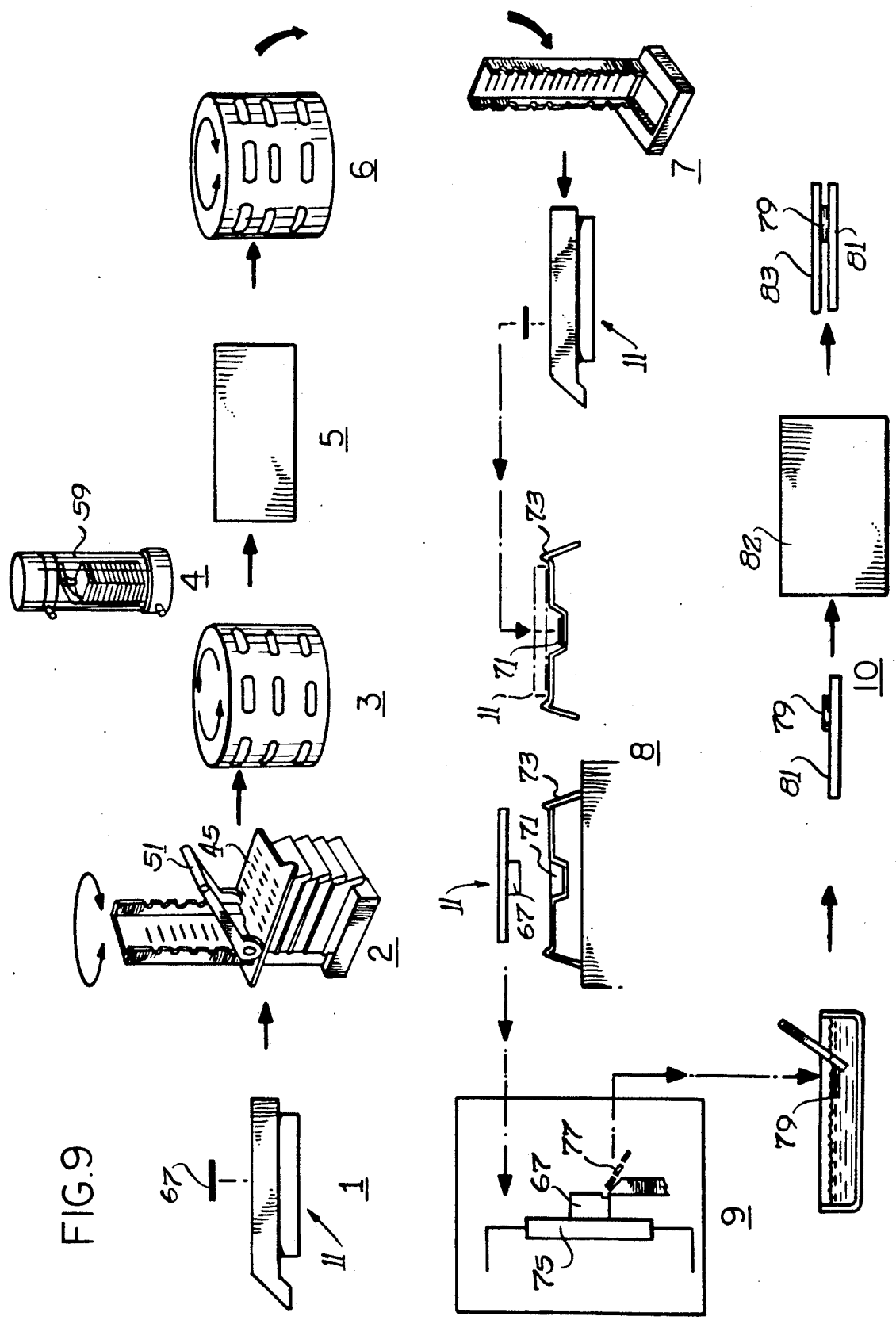

APPARATUS AND METHOD FOR PREPARING TISSUE SAMPLES FOR HISTOLOGICAL EXAMINATION

FIELD OF THE INVENTION

The present invention relates to the preparation of tissue samples for histological examination, and more particularly relates to improved methods and apparatus for treatment of tissue samples prior to embedding the tissue samples in paraffin or the like in preparation for microscopic examination.

BACKGROUND OF THE INVENTION

Standard procedures for preparing tissue samples for microscopic examination involve embedding the tissue sample in paraffin and slicing the paraffin-embedded tissue sample very thinly with a microtome. Prior to embedding the tissue sample, the tissue sample is pretreated in various solutions appropriate to the examination. Typically, prior to paraffin embedding, the tissue sample is fixed, dehydrated, cleared, infiltrated with molten paraffin and, depending on the test, stained. Such prior treatment of the tissue sample requires subjecting the tissue sample to contact with various fluids, including ethanol, zylene, formaldehyde and water.

A histology laboratory processes a large number of tissue samples for examination and it is important that the tissues be prepared as efficiently as possible. A large variety of apparatus has been developed to improve the efficiency of the preparation process. U.S. Pat. No. 3,674,396 to McCormick discloses capsules in which a tissue sample is both prepared for embedding through exposure to various solutions and is then embedded within the capsule. The '396 McCormick patent discloses a process wherein the tissue sample is statically exposed to the various fluids required for preparation of the tissue samples. In the capsules of the '396 McCormick patent, perforated bottom walls are used to retain the tissue samples while providing access to the tissue samples of the various solutions and finally, to molten paraffin.

U.S. Pat. Nos. 4,557,903 and 4,569,647, both to McCormick, disclose improved apparatus for preparing and embedding tissue samples for histological examination. In the '903 McCormick patent, a tissue specimen processing capsule is provided which includes a pair of interlocking frames, each of the frames having a porous web spread across its central opening for holding a tissue specimen in a region divided between the webs. The porous webs permit access to the specimen by processing and impregnating fluids. After the tissue specimen is processed, it is removed from the capsule and placed in a depression of a mold. The empty capsule is placed over the mold depression containing the tissue specimen. Molten paraffin is poured into the mold to fill the depression and to cover the tissue specimen and the porous material of the capsule. The molten paraffin solidifies to form a tissue block with the capsule serving as a clampable base for an outwardly extending, tissue-containing portion.

The '647 McCormick patent discloses an improved method for contacting a tissue specimen with a fluid which is used to treat the tissue specimen. In the '647 McCormick patent, capsules for processing and embedding tissue samples each include a mold, which provides a cavity to receive the tissue sample. The mold has an upper end and a porous or non-porous bottom. The capsule further includes a cover which fits over the open upper end of the mold. The cover includes a frame on which is located a web of porous material intermediate the top and bottom of the frame so that the cover is provided with a recess. The porous web provides access to tissue processing liquids and liquid tissue embedding material, such as paraffin, but prevents passage of any small portions of the tissue specimen which may be generated, thereby preventing cross-contamination of individually capsuled and jointly processed tissue samples. After the tissue samples have been treated with the required fluids, the cover recess above the porous web is at least partially filled with molten paraffin embedding material so that when the embedding material solidifies, the porous web is embedded and the solidified material is thereby formed into a block in the mold. With the porous web and the tissue sample mutually embedded in the block of solidified paraffin, the block is removed from the mold and the cover may be clamped in a microtome and sliced by a microtome blade.

In one embodiment of the '647 McCormick patent, the capsules are adapted to form a stack and the molds are provided with porous bottoms that do not adhere to the embedding paraffin. The stacked capsules provide a passageway running from top to bottom, defined by the molds and cover frames, for passage of a treating fluid in a direction orthogonal to the top and bottom of the capsules. The tissue samples held within the stack capsules are processed by flowing solutions through the passageway formed by the stacked capsules. A molten paraffin embedding material is finally introduced into the stacked capsules. When the stack is separated each tissue sample is embedded in a block of material that is attached to the respective covers.

While apparatus and methods for preparing and embedding tissue samples for histological examination have progressed over the years to provide for efficient methods and apparatus for preparing tissue specimens for histological examination, the large number of tissue samples which are prepared daily by a histological laboratory require the most efficient techniques available to increase the number of samples that can be processed.

Accordingly, it is a principal object of the present invention to provide a cassette for use in the treatment of tissue specimens for histological examination which increases the efficiency of treatment of a fluid specimen by various required fluids.

Another object of the present invention is to provide apparatus for the simultaneous treatment of multiple tissue specimens for histological examination.

Other objects of the invention include providing continuous flow systems and reciprocating flow systems for tissue processing liquids which recycle the various reagents that are used for processing tissue samples and in the economical use of processing cassette components in the final stage of tissue embedding and slicing.

These and other objects of the invention will become more apparent from the following detailed description and the accompanying drawings.

BRIEF DESCRIPTION OF THE DRAWINGS

FIG. 1 is a perspective view of the cassette of the invention;

FIG. 2 is a top view of the cassette of FIG. 1;

FIG. 3 is an enlarged, broken away view of a portion of the cassette of FIG. 2;

FIG. 4 is a perspective view of a frame useful for stacking a plurality of the cassettes of FIG. 1;

FIG. 5 is a side view of the stacking frame of FIG. 4 showing a plurality of the cassettes of FIG. 1 in place;

FIG. 6 is a side view of a stack of cassettes;

FIG. 7 is a sectional view partially broken away of a portion 7 of the stack plates of FIG. 6;

FIG. 8 is a perspective view of a plurality of the cassettes of FIG. 1 loaded into the stacking frame of FIG. 4 and placed into a chamber for use in operation of the method of the invention;

FIG. 9 is a flow diagram showing various steps in the processing of the cassette;

SUMMARY OF THE INVENTION

Figure 10:
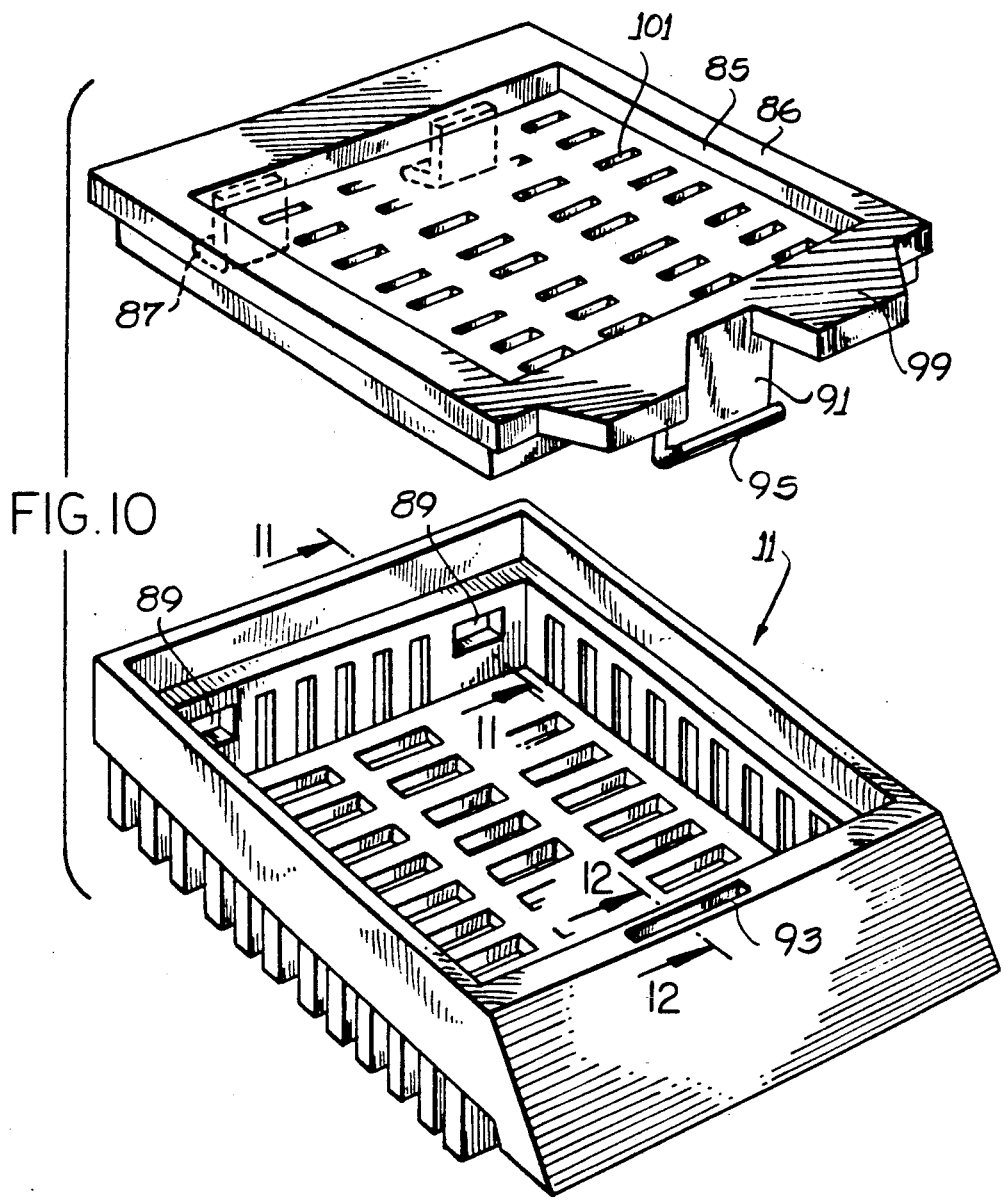
FIG. 10 is a perspective view of a further embodiment of the invention showing a locking cover for the cassette.

The present invention is directed to a stackable cassette for preparation of specimens for histological examination. The cassettes include a bottom wall, two side walls, a front wall and a back wall which define a cavity. The bottom wall has a plurality of apertures disposed therein for passage of fluid through the cassette in a direction orthogonal to the plane of the bottom wall. At least two walls selected from the back wall, two side walls and front wall have a plurality of apertures disposed therein for passage of fluid through the cassette in the direction parallel to the plane of the bottom wall. The selected walls having apertures are preferably opposed walls. In one embodiment of the invention, the cassette further includes a web of porous material disposed over the apertures in the bottom wall and side walls. When the cassettes are placed in stacked relationship the bottom wall of an overlying cassette provides a cover for the underlying cassette.

The invention further includes apparatus for the simultaneous preparation of multiple tissue specimens for histological examination. The apparatus comprises a plurality of cooperating stackable cassettes. Each of the cassettes includes the features described hereinabove. The bottom wall of each overlying cassette in a stacked array providing a top wall or cover for each underlying cassette. The stacked cassettes provide a passageway running from top to bottom defined by the bottom wall of an underlying cassette and the bottom wall of an overlying cassette. The stack of cassettes terminates in a cover provided with a plurality of apertures for passage of the fluid through the stacked. cassettes The tissue specimens held within the stacked cassettes are processed by solutions flowing through the passageway formed by the stacked cassettes and orthogonal to the plane of the bottom wall of the cassettes. The stacked capsules also provide a series of passageways running normal to the plane of the bottom wall whereby solutions may be passed through the cassettes in a direction parallel to the bottom wall. The apertures formed in the sides of the cassette have particular features to assist in the efficient contact of the flowing solutions with the specimens in the cassettes.

Tissue specimen processing may be effected by a continuous flow system or may be effected in a batch system once the cassettes are located in the stacking frame.

DETAILED DESCRIPTION OF THE PREFERRED EMBODIMENT

Illustrated in FIG. 5 is a plurality of the cassettes 11 which have been piled into a continuous stack 13 to provide for processing and embedding of several tissue samples. When stacked together, the cassettes collectively define a continuous passageway which is orthogonal to the plane of a bottom wall. As shown in FIG. 1, the cassette 11 comprises a bottom wall 17, a front wall 19, a back wall 21 and two side walls 23. At least two walls selected from the back wall 21, the front wall 19 and the side walls 23 are provided with a plurality of apertures for passage of fluid through the cassette in a direction parallel to the plane of the bottom wall. Preferably, the selected walls having apertures are opposed walls selected from either the front wall 19 and back wall 21 or the two side walls 23.

The bottom wall is provided with a plurality of apertures 25. As shown in the embodiment in FIG. 1 and FIG. 2, the back wall 21 and front wall 19 are provided with apertures 27 and both of the side walls 23 and the back wall are provided with apertures 29.

As shown in FIG. 1, the top part of each of the front wall 19, back wall 21 and side walls 23 is offset from the wall portions to provide a stacking flange surrounding the walls. The cassettes when placed one atop the other are firmly stacked by means of the stacking flange.

A stacking frame for clamping a plurality of stacks in operating relationship is shown in FIG. 4. The stacking frame 31 includes a base 33 and stanchion 35. The stanchion includes side walls 37, and back wall 39. Slots 41 are provided in back wall 39. The function of slots 41 is explained hereinbelow. The base 33 contains openings in the form of slits 43 or other suitable type of aperture for flow of fluid from a location underlying the base 33.

The base 33 has a well 44 of a size adapted to receive the lower portion of a cassette 11. A series of cassettes are then stacked in operating array upwardly from the base 33. A cover plate is provided to place atop the uppermost cassette. The cover plate 45 contains apertures 47 for passage of fluid therethrough. The underlying surface of the cover plate 45 can also be covered with a porous material. The cover plate 45 includes a tongue 49 which is used to engage the slots 41 in the back wall of stanchion 35 to provide stability to the stacked array of cassettes. A locking handle 51 is provided to lock the cover plate 45 and the stack of cassettes in place. The locking handle 51 includes studs 53 and a cam 55. The studs 53 are engaged with the appropriate semicircular bearing surfaces 52 which are cut out of the side walls 37 of stanchion 35. When the handle is lowered the cam 55 effects a downward thrusting pressure against the cover plate 45.

A porous material, as described in U.S. Pat. No. 4,569,647 to McCormick can be placed over the bottom wall and the upstanding apertured walls of the cassette 11. The porous material may also be placed over the apertures in the cover plate 45. A porous material is used when tissue samples are being processed which may result in fragments of a tissue sample being created which would be of a size sufficiently small to pass through the apertures of the cassette 11 or the cover plate 45. The porous material is a porous fabric, preferably non-woven, which readily passes liquids but retains any tissue fragments. The porous material preferably is a fabric which has a porosity between about 35% and about 65% with a maximum pore size of about 5 microns. A preferred fabric is a non-woven nylon, such as that sold under the trademark Cerex by Monsanto.

After a plurality of cassettes have been loaded into the stacking frame 31 and locked into place by handle 51, the plurality of cassettes is ready for processing. The locked stack of cassettes is adapted to be processed by a number of existing processing technologies. For example, the locked stack of cassettes can be placed into a working container 59 as shown in FIG. 8. A cover 61 is provided for the container for enclosing the locked stack of cassettes into place for treatment with a flow of fluid provided through inlet 63 and outlet 65. Alternatively, the locked stack of cassettes can be placed into a horizontal processor such as an Ames Lab VIP processor. In the horizontal position, the fluid is then adapted for passage in a direction parallel to the bottom wall of cassette 11 through the apertures in the vertical walls of the cassette.

An important embodiment of the invention is illustrated in FIGS. 1, 2 and 3. As shown in these Figures, apertures are formed in all of the side wall, front wall and back wall in the form of elongated, vertically disposed, slots which have particular features. In this embodiment, at least some of the elongated slots are aligned at an angle with respect to the plane of the walls. The slots in the back wall 21 and front wall 19 are at an angle A with relationship to the plane of the back wall. The slots may all be aligned in the same direction. Preferably, the slots on the left side of the back and front wall, as observed from the top view of FIG. 2 are disposed at an angle which faces toward the right side of the cassette. While the slots on the right side are disposed at an angle that faces toward the left side of the cassette. An opposite orientation is also useful, i.e., right hand slots aligned right and left hand slots aligned left. The slots in the side wall 23 are at an angle B which may face either toward the front wall or the back wall of the cassette or may have a split alignment as discussed for the slots in the back wall. While the angles A and B are not particularly critical, it is preferred that these angles be in the range of about 5° to about 45°. By providing angled slots, a swirled or turbulent motion may be imparted to the fluid which is provided within the cassettes when a fluid is caused to pass in a direction parallel to the bottom wall 17 of the cassette 11.

Figure 11:
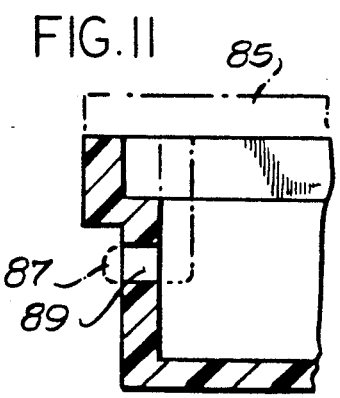
FIG. 11 is a sectional view, partially broken away showing the rear portion of the cassette with the cover locked in place.
Figure 12:
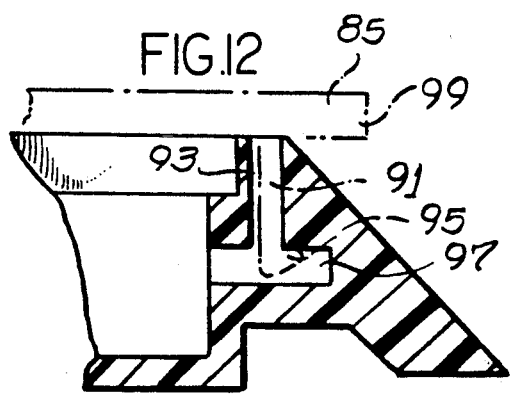
FIG. 12 is a sectional view, partially broken away, of the front portion of the cassette with the cover locked in place.

A further embodiment of the invention is shown in FIGS. 10, 11 and 12. In this embodiment, a separate locking cover 85 is provided for each cassette. The provision of a separate locking cover permits individual handling of single cassettes without employing a stacking frame. The cover 85 comprises lugs 87 which mate with lug restraining means, such as slots 89 in the rear of the cassette. The cover 85 also comprises a locking tab 91 which is inserted through channel 93 in the front of the cassette. The locking tab 91 has a forwardly extending tip 95 which is engaged in a locking recess 97 in the locked position. The locking tab 91 is formed of a resilient material which permits the tip 95 to urge the locking tab 91 away from the forward wall of the channel 93 as the locking tab 91 is inserted in channel 93. The tip 95 has a curvilinear shape to permit disengagement of the cover 85 when upward pressure is applied to handle 99. The cover 85 is provided with apertures 101 to permit the flow of fluids through the cassette, as previously described. The cover 85 has the same offset conformation as the cassette so as to provide a stacking flange 86 extending around the perimeter of the cover. This permits extreme flexibility in the use of the cassettes of the invention in that uncovered and covered cassettes can be stacked in an intermingled and random array.

One type of processing apparatus that is particularly suitable for treatment of tissue specimens utilizing the cassettes of the invention is of a type which provides a washing machine-type action. The stacked cassettes after being locked in frame 31 are placed into a container. The container is provided with a suitable processing fluid and the container is caused to rotate 180° in one direction followed immediately by rotation of 180° in the opposite direction. Such motion provides a component of flow of the processing fluid which is parallel to the bottom wall 17 and also provides a component of flow which is orthogonal to the bottom wall 17 utilizing both of the processing features of the cassette of the present invention.

Referring now to the block diagram, FIG. 9, a tissue specimen 67 is placed into a cassette 11 at station 1. It is preferred that the tissue specimen 67 remain immobilized in the cassette in an orientation most appropriate for microtome slicing and generally, a block of spongy material, (not shown), such as low density polyurethane, is placed over each tissue sample. The labeling area of the cassette 69 is then marked as shown in FIG. 1, the labeling area 69 is on a slanted surface which extends from the front wall 19. The slanted surface 69 extending from the front wall 19 facilitates grasping and placing the cassettes into a stacked array. The slanted surface 69 also provides a larger surface for labeling purposes.

A plurality of cassettes are then stacked together in stacking frame 31 and locked into place utilizing the cover plate 45 and the locking handle 51 as shown at station 2. The locked stack of cassettes may then place into a reciprocating type of processing chamber as shown at station 3 or may be placed into a container 59 for continuous passage of a suitable fluid as shown at station 4. At station 5, a series of processing reagents are placed into the reciprocating container for treatment of the specimen. The cassettes are then removed from the stacking frame as shown at stations 6 and 7. The specimen 67 is removed from the cassette and placed into the well 71 of a mold 73 at station 8. Molten paraffin from a paraffin reservoir (not shown) is placed into the well 71. Prior to hardening of the molten paraffin, the cassette 11 from which the specimen wa removed is placed into the receiving portion of the mold 173 in an overlying relationship to the specimen 67. Additional molten paraffin is poured onto the top of the cassette 11 which causes the cassette to be intimately mated to the specimen when the molten paraffin hardens. The cassette with attached specimen is then removed from the mold and transferred to a microtome slicing section as station 9 which includes a chuck 75 for holding the cassette and a microtome blade 77 for slicing one tissue specimen 67 into tissue sections 79.

As shown at station 10 in the block diagram of FIG. 9, the sliced sections of tissue are then further processed by treatment in a hot water bath placement on a glass slide 81, treatment with reagents at 82 and covering with a second glass slide 83 in accordance with well known tissue processing techniques.

Several advantages of the present invention may now be fully appreciated. The cassettes in which the tissue samples are completely processed, from fixation through embedding and slicing of tissue samples are simple and inexpensive. The cassettes provide flow-through of processing liquids in two directions to facilitate more efficient contact of the treatment fluids with the tissue specimens while providing substantial complete assurance against cross contamination of tissue samples processed in the same solutions. The cassettes are stackable eliminating the need for providing a top cover for each individual cassette. The cassettes provide for processing the tissue specimens with minimal volumes of solutions and for embedding the specimens with a minimum volume of paraffin. The liquid flow system to which the stacked cassettes are particularly adaptable require little technician time. Where desired, the tissue samples may be stained within the cassettes.

While the invention has been described in terms of certain preferred embodiments, modifications obvious to one with ordinary skill in the art may be made without departing from the scope of the invention. Various features of the invention are recited in the following claims.

What is claimed is:

1. A stackable cassette for use in the preparation of specimens for histological examination, said cassette comprising
    an open top container having a bottom wall, two side walls, a front wall and a back wall;
    said bottom wall having a plurality of first apertures disposed therein for passage of fluid through said cassette in a direction orthogonal to the plane of said bottom wall, at least two of said back wall, side walls and front wall having a plurality of second apertures which are elongated vertically disposed slots disposed therein for passage of fluid through said cassette in a direction parallel to the plane of said bottom wall, and
    at least some of said slots being disposed at an angle to the place of said walls to impart a swirled motion to said fluid during passage of fluid through said cassette.

2. A cassette in accordance with claim 1 wherein all of said slots are disposed at an angle to the plane of the respective walls in which the slots are located.

3. A cassette in accordance with claim 1 wherein said second apertures are located in said back wall and said front wall.

4. A cassette in accordance with claim 1 wherein said second apertures are located in said side walls.

5. A method in accordance with claim 1 wherein said second apertures are located in all of said back walls, said front wall and said side walls.

6. A cassette in accordance with claim 5 wherein said angled slots of said back wall and said front wall are disposed at an angle A.

7. A cassette in accordance with claim 6 wherein said angle A is from about 5° to 45°.

8. A cassette in accordance with claim 5 wherein at least some of said second apertures in said side walls are at an angle B.

9. A cassette in accordance with claim 8 wherein said angle B is from about 5° to about 45°.

10. A cassette in accordance with claim 1 wherein a porous material is placed over at least some of the apertures in said cassette.

11. A cassette in accordance with claim 1 having a cover associated therewith, said cover having a plurality of apertures and said cover being adapted to be disposed in a locking relationship with said cassette to provide a closed cassette for individual treatment of a specimen.

12. A cassette in accordance with claim 11 wherein said cover has an offset well in a surrounding peripheral flange which permits stacking of a cassette on top of said cover.

13. Apparatus for the simultaneous preparation of multiple tissue specimens for histological examination comprising
    a plurality of cooperating stackable cassettes, each of said cassettes including a bottom wall, two side walls, a front wall and a back wall, the bottom wall of each overlying cassette in a stacked array providing a top wall for each underlying cassette,
    said bottom wall having a plurality of first apertures disposed therein for passage of fluid through said cassette,
    at least two of said back walls, side walls and front wall having a plurality of second apertures which are elongated vertically disposed slots disposed therein for passage of fluid through said cassette in a direction parallel to the plane of said bottom wall, and
    at least some of said slots being disposed at an angle to the plane of said walls to impart a swirled motion to said fluid during passage of fluid through said cassette.

14. Apparatus in accordance with claim 13 wherein said second apertures are located in at least said back wall and said front wall.

15. Apparatus in accordance with claim 13 wherein said second apertures are located in at least said side walls.

16. Apparatus in accordance with claim 12 wherein said angled slots are disposed in at least the back wall and the front wall and said angled slots on the left side of said back wall and said front wall, viewed from the top, being disposed at an angle A which faces to the right side of said cassette and said angled slots on the right side of said back wall and said front wall, viewed from the top, being disposed at an angle A which faces toward the left side of said cassette.

17. Apparatus in accordance with claim 16 wherein said angle A is from about 5° to 45°.

18. Apparatus in accordance with claim 15 wherein at least some of said second apertures in said side wall are elongated vertical slots which are at an angle B.

19. Apparatus in accordance with claim 18 wherein said angle B is from about 5° to about 45°.

20. Apparatus in accordance with claim 13 having a stacking frame for holding said plurality of stackable cassettes in a stacked and locked array.

21. Apparatus in accordance with claim 20 having a cover for the topmost of said stack of cassettes, said cover having a plurality of apertures.

22. Apparatus in accordance with claim 21 wherein at least one of the intermediate cassettes of said stack of cassettes is provided with a locking cover.

* * * * *